United States Patent
Joo

(10) Patent No.: US 11,497,782 B2
(45) Date of Patent: Nov. 15, 2022

(54) COMPOSITION FOR TREATING ATOPIC DERMATITIS

(71) Applicant: GANGNEUNG-WONJU NATIONAL UNIVERSITY INDUSTRY ACADEMY COOPERATION GROUP, Gangwon-do (KR)

(72) Inventor: Seong-Soo Joo, Gyeonggi-do (KR)

(73) Assignee: GANGNEUNG-WONJU NATIONAL UNIVERSITY INDUSTRY ACADEMY COOPERATION GROUP

( * ) Notice: Subject to any disclaimer, the term of this patent is extended or adjusted under 35 U.S.C. 154(b) by 61 days.

(21) Appl. No.: 16/633,626

(22) PCT Filed: Jul. 24, 2017

(86) PCT No.: PCT/KR2017/007966
§ 371 (c)(1),
(2) Date: Aug. 12, 2020

(87) PCT Pub. No.: WO2019/022263
PCT Pub. Date: Jan. 31, 2019

(65) Prior Publication Data
US 2020/0376053 A1 Dec. 3, 2020

(51) Int. Cl.
A61K 36/03 (2006.01)
A23L 31/00 (2016.01)
A61K 8/9711 (2017.01)
A61P 17/00 (2006.01)
A61K 9/00 (2006.01)

(52) U.S. Cl.
CPC .............. *A61K 36/03* (2013.01); *A23L 31/00* (2016.08); *A61K 8/9711* (2017.08); *A61P 17/00* (2018.01); *A61K 9/0014* (2013.01); *A61K 9/0019* (2013.01); *A61K 9/0053* (2013.01); *A61K 2236/33* (2013.01); *A61K 2236/39* (2013.01)

(58) Field of Classification Search
None
See application file for complete search history.

(56) References Cited

U.S. PATENT DOCUMENTS

2010/0247564 A1   9/2010   Lee et al.

FOREIGN PATENT DOCUMENTS

| KR | 10-14189160000 | 7/2014 |
| KR | 101418916 B1 * | 7/2014 |
| KR | 10-2017-0088551 | 8/2017 |
| WO | 2016-190689 | 12/2016 |

OTHER PUBLICATIONS

Baek et al. (2017) Int. J. Adv. Res. Biol. Sci. 4(4): 120-126. (Year: 2017).*
Jang et al. (2014) Food Sci. Biotechnol. 23(2): 555-560. (Year: 2014).*
Lee et al. (2013) JPP 66: 466-476. (Year: 2013).*
Li et al. (2017) Mar. Drugs 15, 49 (15 pages) (Year: 2017).*
Luo et al. (2010) J. Med. Plant Res. vol. 4(8): 2557-2565. (Year: 2010).*
Ye et al. (2009) Eur. Food Res. Technol. 230: 101-109. (Year: 2009).*
Kim et al. (2012) Cancer Prev. Res. 17: 169-175. (Year: 2012).*
Kim, et al. "Effect of Hizikia fusif orme Extracts on Serum Lipid Profile and Anti-inflammatory Effects of the Rat" Cancer Prevention Research, 2012, 17, 169-175.

* cited by examiner

*Primary Examiner* — Russell G Fiebig
(74) *Attorney, Agent, or Firm* — Stuart H. Mayer; Mayer & Williams PC

(57) ABSTRACT

The present invention provides a composition for treating atopic dermatitis, the composition containing, as an active ingredient, a butanol fraction of an *S. fusiforme* extract.

4 Claims, 14 Drawing Sheets
Specification includes a Sequence Listing.

COMPOSITION FOR TREATING ATOPIC DERMATITIS

TECHNICAL FIELD

The present invention relates to a composition for treating atopic dermatitis, and more particularly, to an atopic dermatitis-treating composition having, as an active ingredient, a butanol fraction of Sargassum fusiforme (S. fusiforme).

BACKGROUND ART

Atopic dermatitis (AD) refers to a chronic inflammatory skin disease caused by interaction between a helper T cell (Th2) which produces a type 2 cytokine and an immunoglobulin E (IgE) antibody. The disease is caused by an inappropriate immune response to hypersensitivity inflammation reaction triggered by external stimuli. An initial stage of atopic dermatitis development is induced by an activated Th2-type cell having allergen specificity while, as the development progresses, Th1 cytokines including interleukin 2 (IL-2) and interferon γ (IFN-γ) are expressed, which results in atopic dermatitis becoming chronic, severe and intractable. As atopic dermatitis caused by an inflammatory reaction is a non-contagious chronic and recurrent skin condition, various skin disorders can be accompanied. Over the recent 10 years, a variety of research on atopic dermatitis has been conducted. As the existing research has found that allergic inflammation accompanying various immune disorders is known as the common cause of atopic dermatitis, the most effective anti-atopic dermatitis medication needs to have an immunosuppressive function, capable of controlling the imbalance of Th1/Th2 cells and, at the same time, be safe to the human body with no recurrence during the long-term treatment. Currently, the most common topical immunosuppressants for atopic dermatitis are corticosteroids, cyclosporine A, tacrolimus, pimecrolimus, etc. However, as there has been a growing concern about the long-term use of such immunosuppressants on the grounds of their limited effects; or the risks of the side effects, such as lymphoma, much research on effective prophylactic or therapeutic agent of atopic dermatitis derived from natural sources is being carried out. In this regard, a prophylactic and therapeutic composition for atopic dermatitis having an S. fusiforme extract as an active ingredient is disclosed in Korean Patent No. 1418916.

DISCLOSURE OF THE INVENTION

Technical Problem

However, the related art has problems in that hexane fractions are included in the process of extraction, and thus using the composition of the related art as a prophylactic or therapeutic composition for atopic dermatitis may cause regulatory problems, and in that the content of the active ingredient is low.

The present invention has been made to solve various problems including the above problems, and an object of the present invention is to provide a composition for treating atopic dermatitis by utilizing S. fusiforme which can be more effectively and economically mass-produced. However, the object is for illustration purpose only and the scope of the present invention is not limited thereby.

Technical Solution

According to an aspect of the present invention, provided is a pharmaceutical composition for treating atopic dermatitis comprising, as an active ingredient: a butanol fraction of an S. fusiforme extract; an ethyl acetate fraction obtained from an ethyl acetate layer which has been further fractionated with ethyl acetate from a water layer fractionated with n-hexane and water; or chromatographic fractions corresponding to Rf values 0.3-0.9 on thin layer chromatography (TLC) carried out with n-hexane and ethyl acetate (8:2) as a mobile phase, among fractions prepared by the chromatography of the ethyl acetate fraction.

According to another aspect of the present invention, provided is a method of treating atopic dermatitis in a subject suffering from atopic dermatitis comprising administering a therapeutically effective dose of the pharmaceutical composition to the subject.

According to another aspect of the present invention, provided is a nutraceutical composition used for alleviating atopic dermatitis comprising, as an active substance: a butanol fraction of an S. fusiforme extract; an ethyl acetate fraction obtained from an ethyl acetate layer which has been further fractionated with ethyl acetate from a water layer fractionated with n-hexane and water; or chromatographic fractions corresponding to Rf values 0.3-0.9 on thin layer chromatography (TLC) carried out with n-hexane and ethyl acetate (8:2) as a mobile phase, among fractions prepared by the chromatography of the ethyl acetate fraction.

According to another aspect of the present invention, provided is a cosmetic composition for alleviating atopic skin comprising, as an active substance: a butanol fraction of an S. fusiforme extract; an ethyl acetate fraction obtained from an ethyl acetate layer which has been further fractionated with ethyl acetate from a water layer fractionated with n-hexane and water; or chromatographic fractions corresponding to Rf values 0.3-0.9 on thin layer chromatography (TLC) carried out with n-hexane and ethyl acetate (8:2) as a mobile phase, among fractions prepared by the chromatography of the ethyl acetate fraction.

According to another aspect of the present invention, provided is a method of preparing an ethyl acetate fraction of an S. fusiforme extract having improved atopic dermatitis treatment effects, the method including: i) preparing S. fusiforme lower alcohol extract by extracting S. fusiforme with lower alcohol having 1 to 4 carbon atoms or an aqueous solution thereof; ii) fractionating the S. fusiforme lower alcohol extract with n-hexane after dissolving the S. fusiforme lower alcohol extract into water; iii) fractionating a water layer fractionated in the step ii with ethyl acetate; and iv) preparing ethyl acetated fraction of S. fusiforme extract by removing ethyl acetate from a fractionated ethyl acetate layer in the step iii.

Advantageous Effects

According to an embodiment of the present invention as described above, an S. fusiforme-derived active ingredient having an anti-atopic dermatitis efficacy can replace the conventional atopic dermatitis topical immunosuppressants, and thus can be utilized as an atopic dermatitis therapeutic agent. However, the scope of the present invention is not limited by such an effect.

MODE FOR CARRYING OUT THE INVENTION

Definition of Terms

Figure 1:
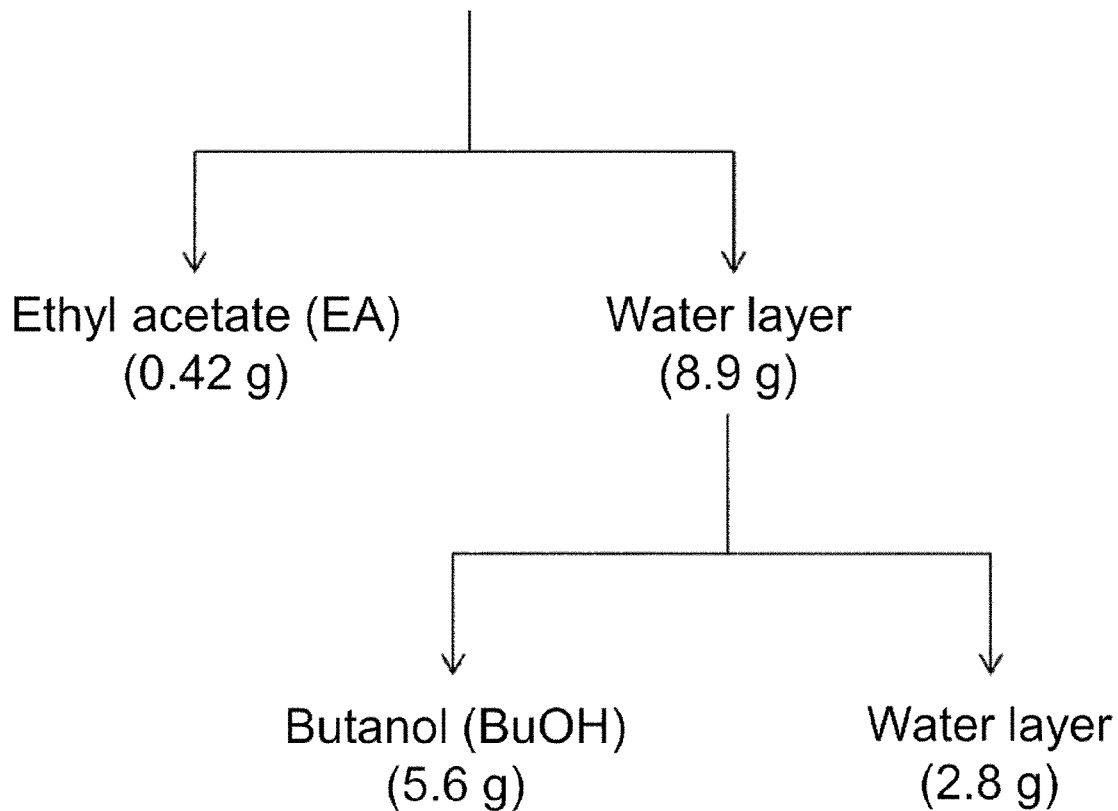
FIG. 1 is a schematic diagram illustrating a solvent-extraction process by using an S. fusiforme ethanol extract according to an embodiment of the present invention.

As used herein, the term "*Sargassum fusiforme (S. fusiforme)*" refers to a type of brown seaweed which is widely spread in Korea, Japan, China and the like, and commonly seen along rocky shores, and known for having pharmacological efficacy in various aspects including anti-cancer treatment, immunoregulation, anti-inflammation and anti-oxidation.

As used herein, the term "DPPH radical" refers to one of the organic nitrogen radicals having a deep violet color, and, in general, is used as a reagent to assess the free radical scavenging activity of various antioxidant substances. In addition, since DPPH is a stable free radical, which plays a role in receiving electrons or hydrogen radicals to become a stable diamagnetic molecule, the DPPH radical was used for the analysis of radical scavenging activity to evaluate, at an initial stage, the anti-oxidant effects of an *S. fusiforme* extract according to the present invention.

As used herein, the term "Raw 264.7 cell" refers to a murine macrophage cell line. Activity in lipopolysaccharide (LPS)-stimulated Raw 264.7 cell is initiated by the signaling of toll-like receptor-4, and induces inflammation through NF-κB signaling pathway. This process induces the production of nitrogen oxide (NO) and prostaglandin E2 (PGE2) and secretes multiple cytokines including proinflammatory cytokines TNF-α, IL-1β and IL-6.

DETAILED DESCRIPTION OF THE INVENTION

According to an aspect of the present invention, provided is a pharmaceutical composition for treating atopic dermatitis comprising, as an active substance: a butanol fraction of an *S. fusiforme* extract; an ethyl acetate fraction obtained from an ethyl acetate layer which has been further fractionated with ethyl acetate from a water layer fractionated with n-hexane and water, or chromatographic fractions corresponding to Rf values 0.3-0.9 on thin layer chromatography (TLC) carried out with n-hexane and ethyl acetate (8:2) as a mobile phase, among fractions prepared by the chromatography of the ethyl acetate fraction.

In regard to the pharmaceutical composition, the butanol fraction of the *S. fusiforme* extract can be prepared by a method including: i) preparing *S. fusiforme* lower alcohol extract by extracting *S. fusiforme* with lower alcohol having 1 to 4 carbon atoms or an aqueous solution thereof; ii) fractionating the *S. fusiforme* lower alcohol extract with ethyl acetate after dissolving the *S. fusiforme* lower alcohol extract into water; iii) fractionating a water layer fractionated in the step ii with butanol; and iv) preparing a butanol fraction by removing butanol from a fractionated butanol layer in the step iii.

In regard to the pharmaceutical composition, the volume ratio of the aqueous solution of the *S. fusiforme* lower alcohol extract to the ethyl acetate may be 1 to 0.5-2 while the volume ratio of the water layer to the butanol may be 1 to 0.5-2.

In regard to the pharmaceutical composition, the ethyl acetate fraction can be prepared by a method including: i) preparing *S. fusiforme* lower alcohol extract by extracting *S. fusiforme* with lower alcohol having 1 to 4 carbon atoms or an aqueous solution thereof; ii) fractionating the *S. fusiforme* lower alcohol extract with n-hexane after dissolving the *S. fusiforme* lower alcohol extract into water; iii) fractionating a water layer fractionated in the step ii with ethyl acetate; and iv) preparing ethyl acetated fraction of *S. fusiforme* extract by removing ethyl acetate from a fractionated ethyl acetate layer in the step iii.

In regard to the pharmaceutical composition, the volume ratio of the aqueous solution of the *S. fusiforme* lower alcohol extract to the n-hexane may be 1 to 0.5-2 while the volume ratio of the water layer to the ethyl acetate may be 1 to 0.5-2.

According to another aspect of the present invention, provided is a method of treating atopic dermatitis in a subject suffering from atopic dermatitis comprising administering a therapeutically effective dose of the above-described pharmaceutical composition to the subject.

In regard to the method, the administering may be performed by include oral, intravenous, intramuscular or transdermal administration.

According to another aspect of the present invention, provided is a nutraceutical composition used for alleviating atopic dermatitis comprising, as an active substance: a butanol fraction of an *S. fusiforme* extract; an ethyl acetate fraction obtained from an ethyl acetate layer which has been further fractionated with ethyl acetate from a water layer fractionated with n-hexane and water; or chromatographic fractions corresponding to Rf values 0.3-0.9 on thin layer chromatography (TLC) carried out with n-hexane and ethyl acetate (8:2) as a mobile phase, among fractions prepared by the chromatography of the ethyl acetate fraction.

According to another aspect of the present invention, provided is a cosmetic composition for alleviating atopic skin comprising, as an active substance: a butanol fraction of an *S. fusiforme* extract; an ethyl acetate fraction obtained from an ethyl acetate layer which has been further fractionated with ethyl acetate from a water layer fractionated with n-hexane and water; or chromatographic fractions corresponding to Rf values 0.3-0.9 on thin layer chromatography (TLC) carried out with n-hexane and ethyl acetate (8:2) as a mobile phase, among fractions prepared by the chromatography of the ethyl acetate fraction.

According to another aspect of the present invention, provided is a method of preparing an ethyl acetate fraction of an *S. fusiforme* extract having improved atopic dermatitis treatment effects, the method including: i) preparing *S. fusiforme* lower alcohol extract by extracting *S. fusiforme* with lower alcohol having 1 to 4 carbon atoms or an aqueous solution thereof; ii) fractionating the *S. fusiforme* lower alcohol extract with n-hexane after dissolving the *S. fusiforme* lower alcohol extract into water; iii) fractionating a water layer fractionated in the step ii with ethyl acetate; and iv) preparing ethyl acetated fraction of *S. fusiforme* extract by removing ethyl acetate from the fractionated ethyl acetate layer in the step iii.

The method can further comprises fractionating by removing a solvent after collecting chromatographic fractions corresponding to Rf values 0.3-0.9 on thin layer chromatography (TLC) carried out with n-hexane and ethyl acetate (8:2) as a mobile phase, among fractions prepared by the chromatography of the ethyl acetate fraction.

Even though this applicant applied for a patent regarding a prophylactic or therapeutic composition for atopic dermatitis having an *S. fusiforme* extract as an active ingredient (Korean Patent No. 1418916), the patent has problems in that hexane fractions are included in the process of extraction, and thus using the composition for the treatment of atopic dermatitis may cause regulatory problems, and in that the content of the active ingredient exhibiting anti-atopic efficacy is low. However, the applicant has made intensive efforts to solve the above problems and finally succeeded in more simply preparing a secondary fraction of an *S. fusiforme* extract capable of increasing the content of butanoic acid which is an anti-atopic dermatitis active ingredient of the *S. fusiforme* extract, by excluding a hexane process from an *S. fusiforme* extract fractionation process. Accordingly, the anti-atopic dermatitis active ingredient having high content of the butanol can replace the conventional topical immunosuppressants for atopic dermatitis.

Hereinafter, the present invention will be described in more detail through examples. However, the present invention is not limited to these examples described below, but may be implemented in various other forms, and the following examples are provided to complete the disclosure of the present invention and to fully disclose the scope of the invention to those skilled in the art.

Example 1: Preparation of *S. fusiforme* Extract 1-1: *S. fusiforme* Solvent Extraction and Fraction Preparation

*S. fusiforme* used in the present invention was collected in October 2015 and used after washing out salt and sand from the collected *S. fusiforme* with tap water, sterilizing the washed *S. fusiforme* with 80% ethanol, washing the sterilized *S. fusiforme* with distilled water and freeze-drying the washed *S. fusiforme*. The dried *S. fusiforme* powder (100 g) grinded from the freeze-dried *S. fusiforme* was immersed into 1 L of 80% ethanol, and extracted for 3 days every 24 hours at a room temperature. For improving the extraction method above, 10 g of freeze-dried powder extracted from the 80% ethanol was dissolved in 1 L of distilled water, and diluted with the ethanol extract in the distilled water and ethyl acetate (volume ratio=1:1) for performing a primary fractionation, and then, among a water layer and an ethyl acetate layer fractionated from the ethyl acetate, the water layer was fractionated and added with butanol, the same volume as the water, for performing a secondary fractionation, which resulted in the obtainment of an ethyl acetate fraction (EA), a butanol fraction (BuOH) and residues (water fraction), with a yield of the ethyl acetate fractionation, the primary water fraction, the butanol fraction and the secondary water fraction being 4.2%, 89%, 56% and 28% respectively (FIG. 1).

1-2: *S. fusiforme* Ethyl Acetate Fraction Preparation

Figure 18:
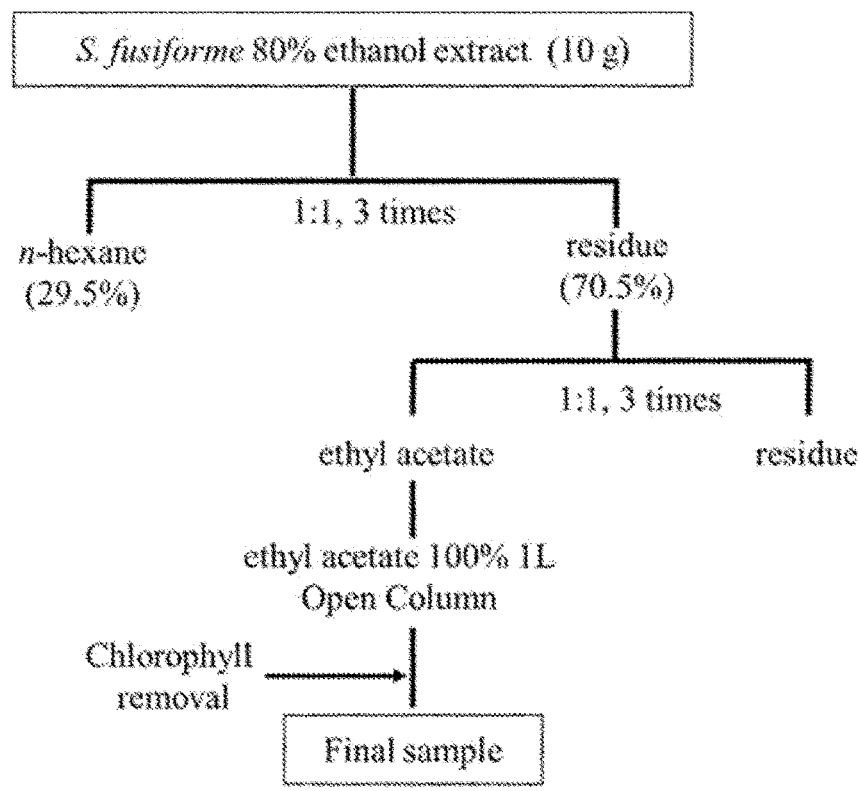
FIG. 18 is a view illustrating an improved separation process of an active ingredient of *S. fusiforme* for improving the anti-atopic dermatitis effects of *S. fusiforme*.
Figure 19:
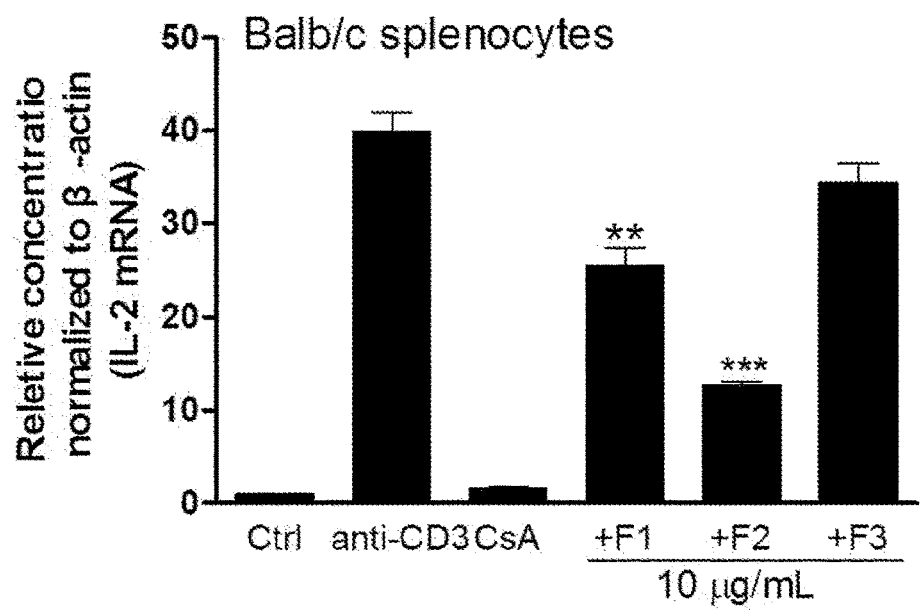
FIG. 19 is a graph analyzing the expression of IL-2mRNA to identify the anti-atopic dermatitis effects of a final sample (an F2 fraction) obtained according to the improved separation process above.
Figure 20:
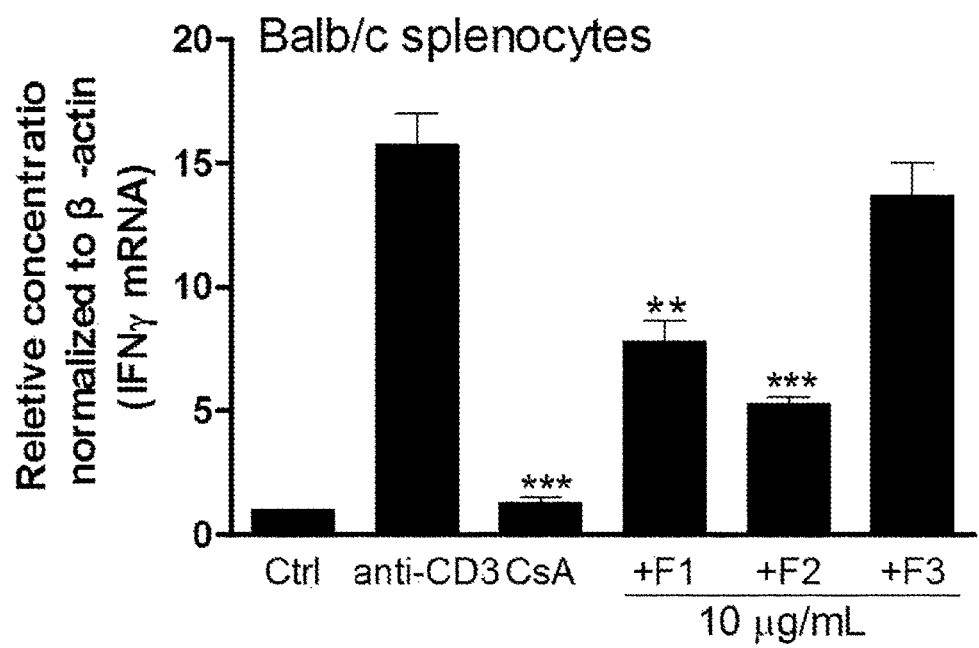
FIG. 20 is a graph analyzing the expression of IFNγ mRNA to identify the anti-atopic dermatitis effects of a final sample (an F2 fraction) obtained according to the improved separation process above.
Figure 21:
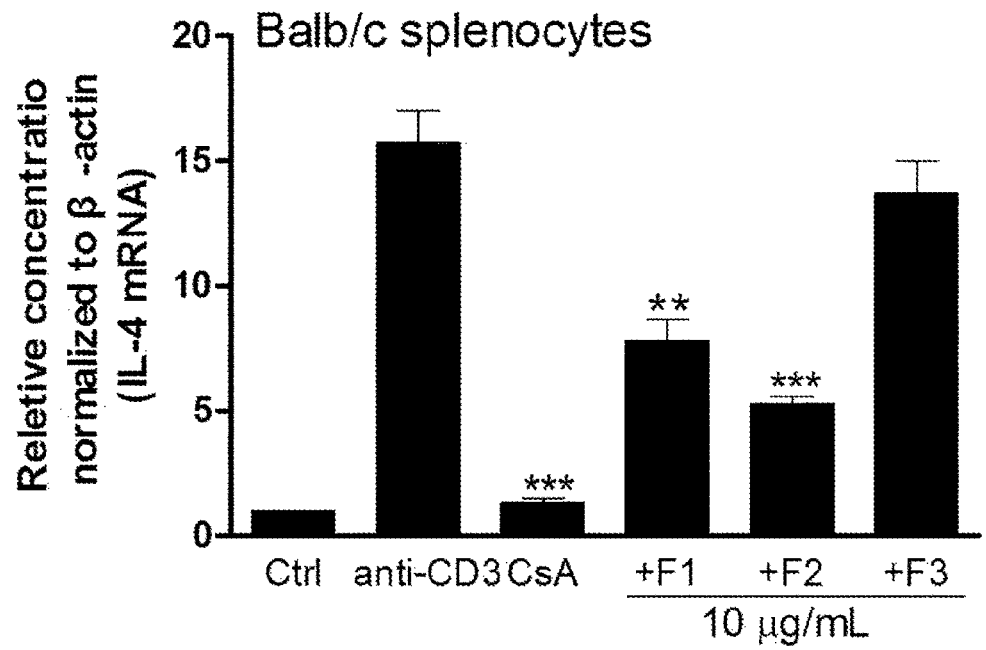
FIG. 21 is a graph analyzing the expression of IL-4 mRNA to identify the anti-atopic dermatitis effects of a final sample (an F2 fraction) obtained according to the improved separation process above.
Figure 22:
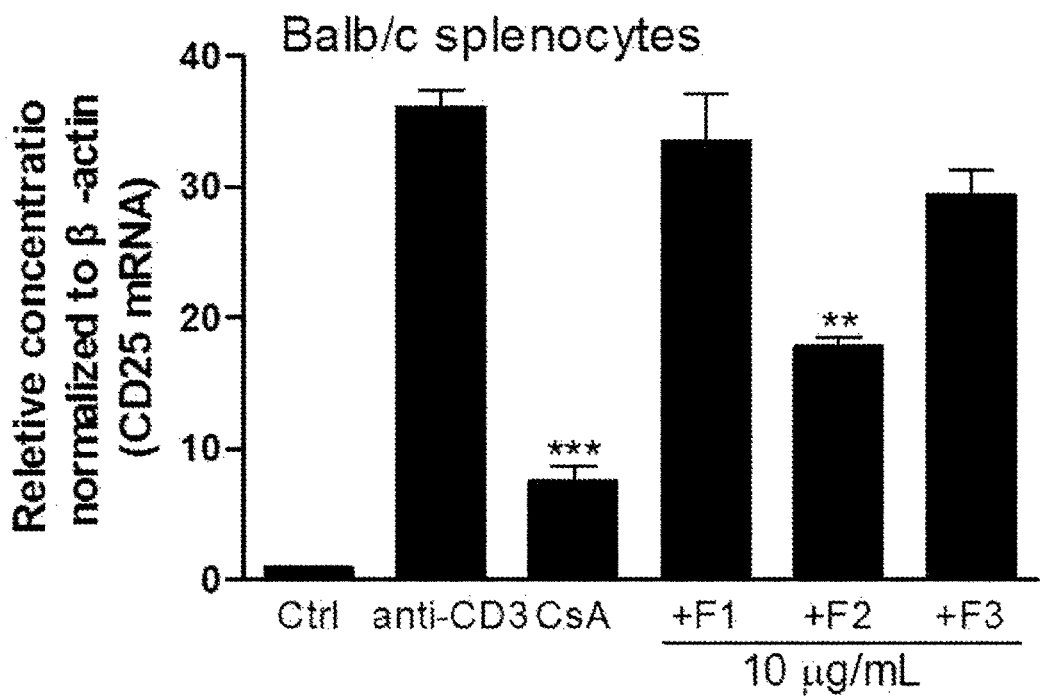
FIG. 22 is a graph analyzing the expression of CD25 mRNA to identify the anti-atopic dermatitis effects of a final sample (an F2 fraction) obtained according to the improved separation process above.
Figure 23:
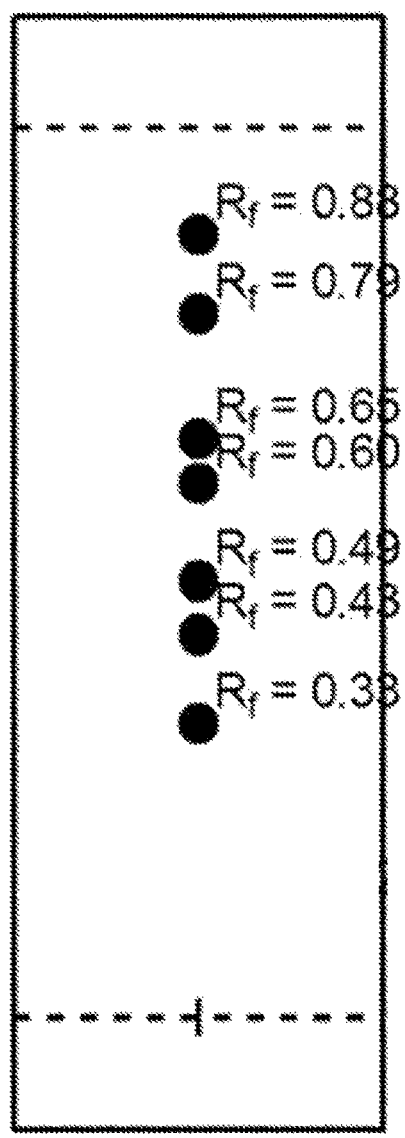
FIG. 23 is a graph illustrating Rf values in the thin-layer chromatography (TLC) results of an F2 fraction conducted through an open column chromatography according to the improved separation process in FIG. 18.

For improving the anti-atopic dermatitis efficacy of an *S. fusiforme* extract according to the present invention, after 10 g of an 80% ethanol extract was fractionated three times with n-hexane (n-hexane:water=1:1, residues thereof were fractionated again with ethyl acetate (ethyl acetate:water=1:1). Then, to remove a large amount of chlorophyll contained in the *S. fusiforme* extract, 1 L of 100% ethyl acetate was used to conduct an open column chromatography on a silica gel 60 (230-400 mesh) (FIG. 18).

Example 2: Gas Chromatography-Mass Spectrometry (GC-MS) Analysis

All the above specimens obtained, according to an embodiment of the present invention, were dissolved in methanol and analyzed by the Agilent 5975C GC/MS system (Agilent Technologies, US) while chromatographic separation was conducted by using a helium carrier gas and an HP-5 column (250 μm×0.25 μm×30 m, Agilent Technologies, US). Specifically, 1 μL of each specimen was inserted into an injector and an injection mode is a split mode with a ratio of 5:1 while a column flow was set at 5 mL/min and 1 mL/min, respectively. The temperature of the injector and a transfer line were both set at 250° C. while the temperature of a GC oven was maintained at 50° C. for 3 minutes, and then increased by 10° C./min from 50° C. to 280° C. In addition, the temperature of an ion source was set at 250° C. and ionization energy was fixed at −70 V. The analysis results were collected every 4 minutes within a range of 35-250 m/z under 1059 V and separated components were analyzed by comparing the same with Wiley 7n library data in terms of retention time and mass spectra.

Figure 2:
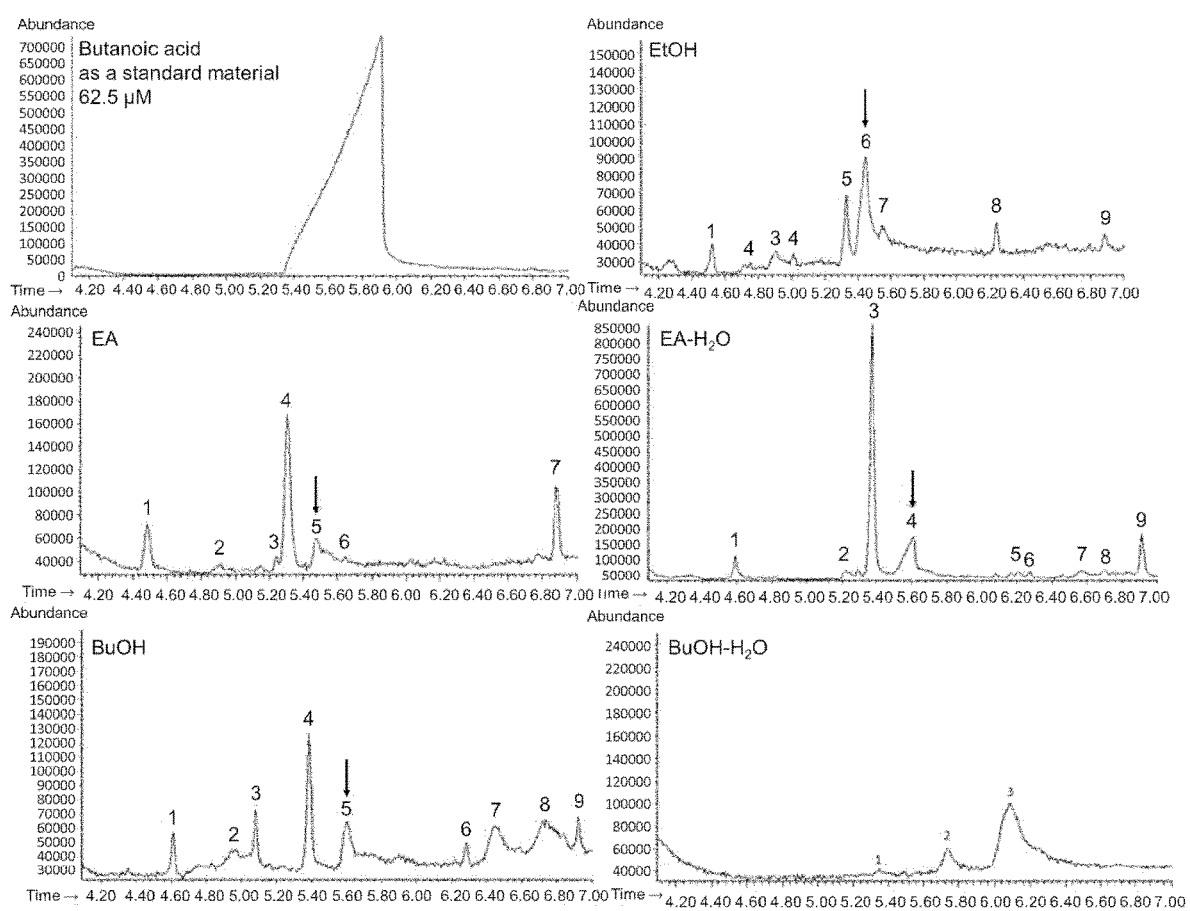
FIG. 2 is a graph illustrating the gas chromatography mass spectrometry (GC-MS) analysis results of an *S. fusiforme* fraction according to an embodiment of the present invention.

According to the GC-MS analysis results, various ingredients of each fraction were found within a retention time of 4.154-21.706 minutes, and according to the results after comparing areas of 4.154-7 minutes which were a reference material detection time, in order to identify the relative amount of butanoic acid which each fraction contained, all fractions except for the secondary water fraction were found to contain butanoic acid, and contain an ethanol extract (25%), an ethyl acetate fraction (9%) and a butanol fraction (10%), such that this resulted the improvement of a method for obtaining a fraction containing a butanoic acid expected to be an anti-atopic efficacy of *S. fusiforme* (FIG. 2).

Example 3: Radical Scavenging Activity and Protein Protection Assay 3-1: Radical Scavenging Activity According to an embodiment of the present invention, a radical scavenging activity analysis was conducted by using a DPPH radical in order to evaluate, at an initial stage, the anti-oxidant efficacy of an *S. fusiforme* fraction.

In order to evaluate free radical scavenging activity, firstly the above fraction was reacted with a DPPH solution (Espin, J. C. et al., *J. Agric. Food Chem.*, 48:648-656, 2000), the freeze-dried fraction as a stock solution (100 mg/mL) was dissolved with DMSO (dimethyl sulfoxide, Sigma-Aldrich, US), and each fraction (ethanol (EtOH), ethyl acetate (EA), ethyl acetate-water (EA-$H_2O$), butanol (BuOH) and butanol-water (BuOH—$H_2O$)) was reacted with 0.3 mM of DPPH solution dissolved in methanol. A pre-determined concentration (100 μg/mL) of each fraction was reacted in the DPPH radical solution for 20 minutes at room temperature, and then the absorbance of the same was evaluated at a wavelength of 517 nm. The DPPH free radical scavenging activity (%) was calculated by using the equation below, and 0.1 mM of ascorbic acid was used as a positive control while 10% DMSO was used as a negative control (vehicle control). In the equation below, Ac represents the absorbance of a specimen of the DPPH solution, the control group, A represents the absorbance of a specimen in the DPPH solution, and As represents the absorbance of a specimen itself.

$$\text{DPPH radical scavenging activity } (\%) = [Ac-(A-As)]/Ac \times 100.$$

Figure 3:
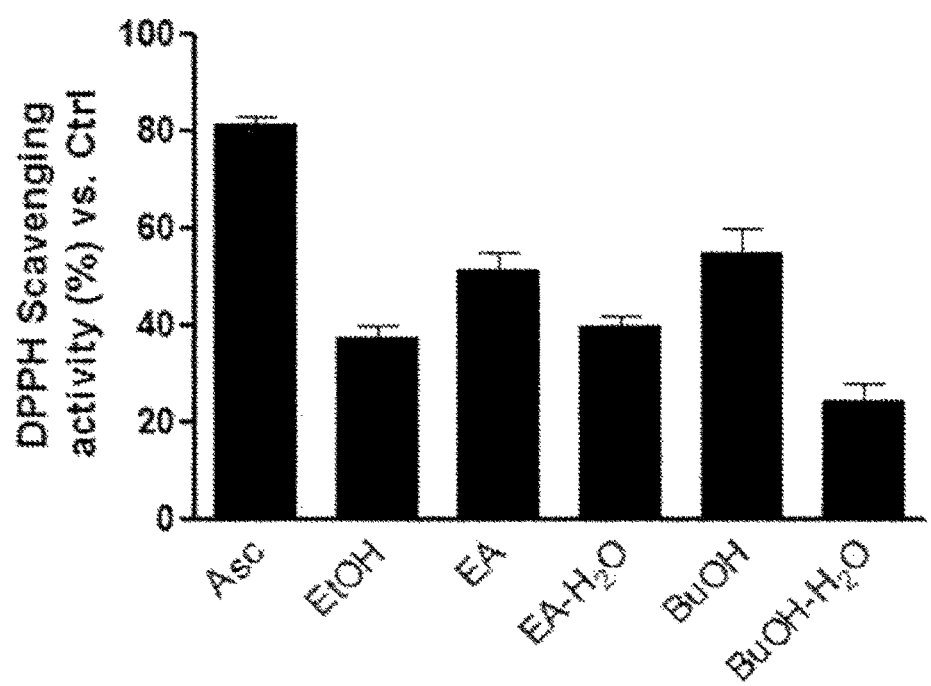
FIG. 3 is a graph illustrating the analysis results of radical scavenging activity from an *S. fusiforme* fraction according to an embodiment of the present invention.

According to the results of the DPPH analysis, each fraction of *S. fusiforme* showed radical scavenging activity at 100 μg/mL and reached a high level of radical scavenging activity in the ethyl acetate and butanol fractions, which means the anti-oxidant efficacy of *S. fusiforme* among biological activities thereof and accordingly indicates that fractionation extraction was well conducted (FIG. 3). As shown in FIG. 3, the radical scavenging activity of ethyl acetate and butanol was similar but they were excluded in other subsequent experiments because of a low yield of ethyl acetate meaning a low degree of economic calculability.

3-2: Protein Protection Assay

In order to conduct a protein protection assay for the *S. fusiforme* extract according to an embodiment of the present invention, hydroxyl radical-mediated oxidation experiments were performed by using a metal-catalyzed reaction with some modifications made to the previously reported method (Mayo, J. C. et al., *Biochim Biophys. Acta.*, 1620: 139-150, 2003). Specifically, a target protein, bovine serum albumin (BSA) was dissolved in a 150 mL phosphate buffer (p 7.3) until the final concentration of the target protein reached 0.5 mg/mL, and a different concentration of fractions and ascorbate (Asc) in amount of 6.25-100 μg/mL each were added into the BSA solution, followed by the incubation of the BSA solution in the presence or absence of 100 μM copper ($Cu^{2+}$) and 2.5 mM $H_2O_2$. 0.1 mM of ascorbate dissolved in phosphate buffered saline (PBS) was used as a control antioxidant while relatively 0.1 mM of ascorbic acid was used as positive control and 10% DMSO was used as a vehicle control.

The reaction was carried out in an open tube with no lid and placed in a shaking water bath of which temperature was maintained at 37° C., and all reactants including BSA were incubated for 2 hours. After the reaction was complete, each mixture above was separated on a 10% sodium dodecyl sulfate-polyacrylamide gel electrophoresis (SDS-PAGE), and stained with 0.1% Coomassie Blue solution for visualizing the protein.

Figure 4:
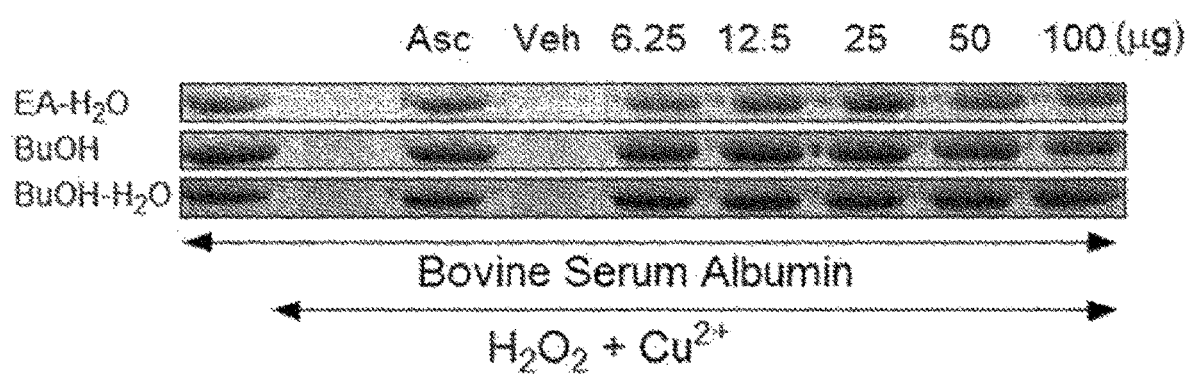
FIG. 4 is a gel photograph illustrating the protein protection assay results of an *S. fusiforme* fraction according to an embodiment of the present invention.

As a result, each fraction of all concentrations showed anti-oxidant activity as much as a protein capable of perfectly preventing BSA proteolysis from the attack of hydroxyl free radicals produced by $Cu^{2+}$ and $H_2O_2$ (FIG. 4). Therefore, it has been confirmed that each extract is capable of effectively scavenging free radicals including DPPH and hydroxyl free radicals, which demonstrates those extracts having the efficacy of effectively removing, through anti-oxidant effect, oxidants which exacerbate atopic-dermatitis and the like.

Example 4: Anti-Inflammatory Activity Analysis 4-1: Nitric Oxide Production Measurement In order to more closely examine the anti-oxidant effects of the *S. fusiforme* fraction according to an embodiment of the present invention, the level of nitric oxide from Raw 264.7 which is murine macrophage cell line, was measured.

Specifically, Raw 264.7 cells (1×10$^6$ cell/mL) were dispensed to a 24-well tissue culture plate, and pre-incubated at a temperature of 37° C. for 12 hours for the cells to be stably attached. Then, the cells were washed with PBS, and incubated for 24 hours after 1% FBS DMEM containing samples [lipopolysaccharide (LPS), each fraction (50 μg/mL)] was refilled. The production of nitric oxide was measured by measuring the amount of nitrate in the media with the use of a griess reagent (Promega). As the nitric oxide production suppression effect by each fraction was measured in the Raw 264.7 cell line, to stimulate the production of nitric oxide, 1 μg/mL of LPS was added and the cells were treated with 50 μg/mL of each fraction for 24 hours.

Figure 5:
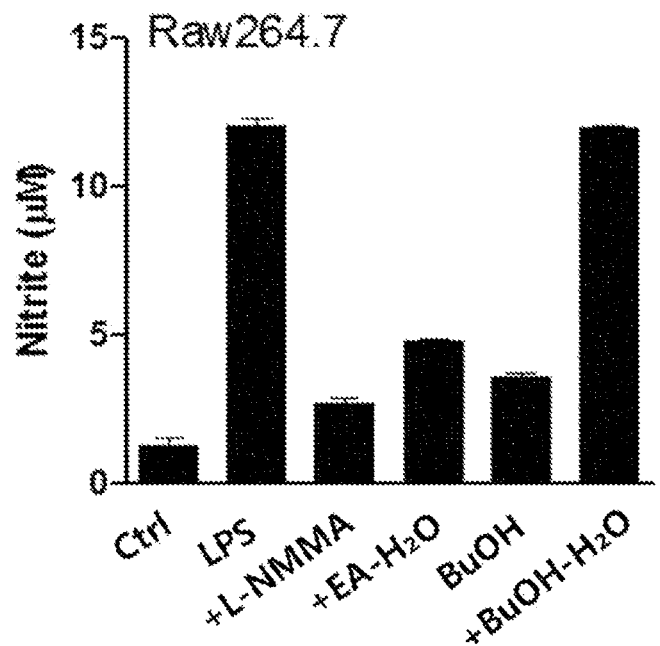
FIG. 5 is a graph illustrating the suppression of nitric oxide production by an *S. fusiforme* fraction according to an embodiment of the present invention.
Figure 6:
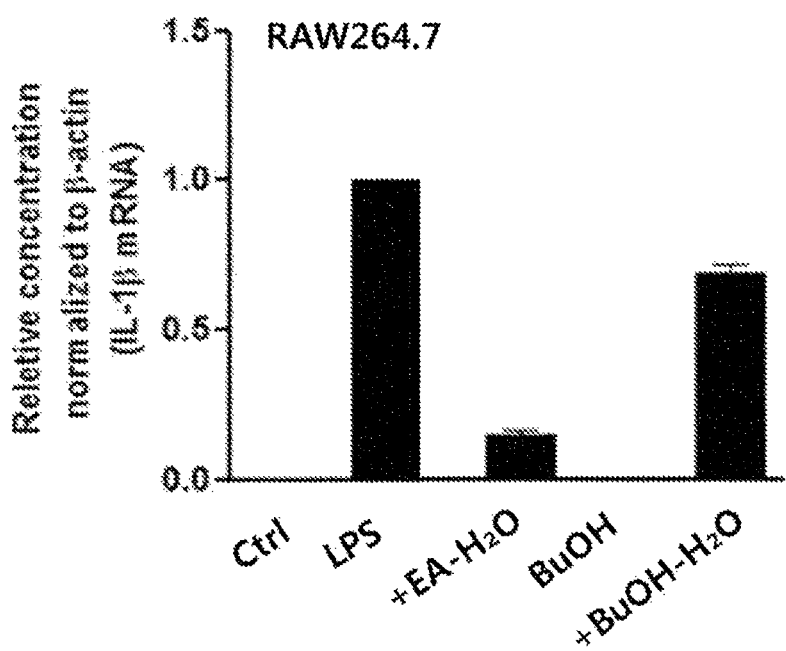
FIG. 6 is a graph which is obtained by observing the anti-inflammatory activity of an *S. fusiforme* fraction, and which demonstrates a decrease in the expression of a proinflammatory cytokine, IL-1β in Raw 264.7 cells according to an embodiment of the present invention.
Figure 7:
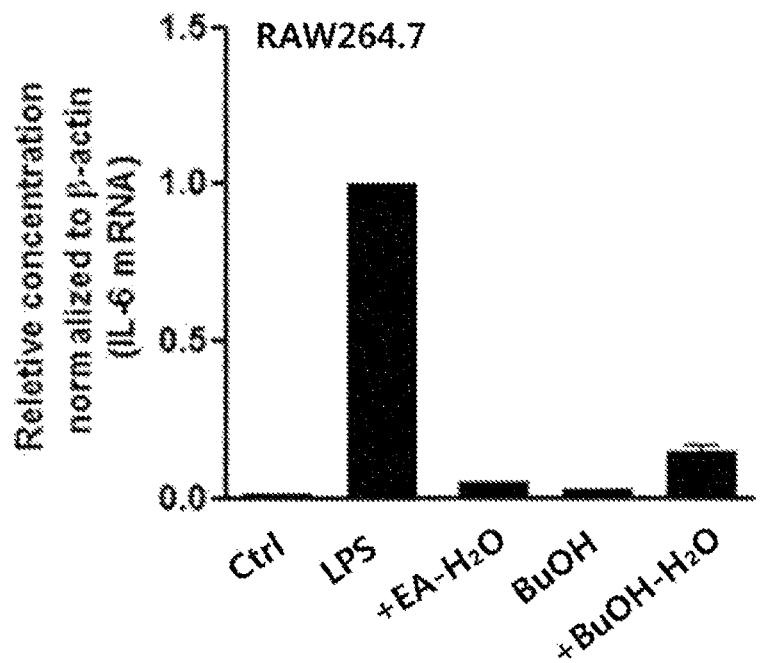
FIG. 7 is a graph which is obtained by observing the anti-inflammatory activity of an *S. fusiforme* fraction, and which demonstrates a decrease in the expression of a proinflammatory cytokine IL-6 in Raw 264.7 cells according to an embodiment of the present invention.
Figure 8:
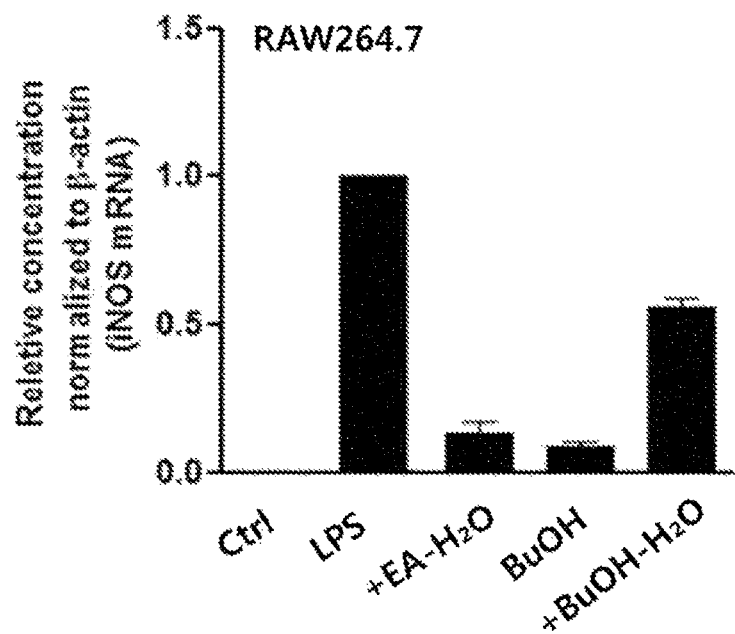
FIG. 8 is a graph which is obtained by observing the anti-inflammatory activity of an *S. fusiforme* fraction, and which demonstrates a decrease in the expression of a proinflammatory cytokine TNF-α in Raw 264.7 cells according to an embodiment of the present invention.
Figure 9:
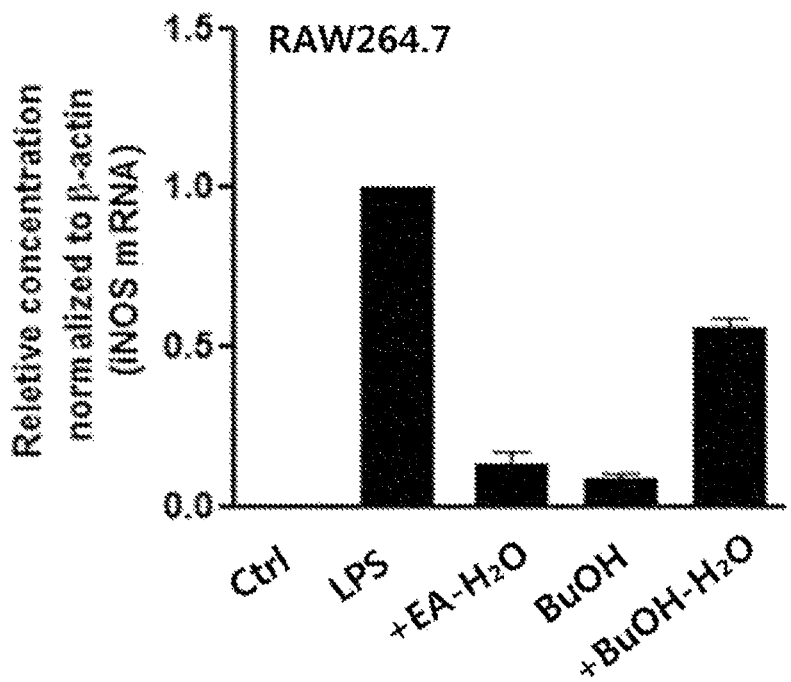
FIG. 9 is a graph which is obtained by observing the anti-inflammatory activity of an *S. fusiforme* fraction, and which demonstrates the expression inhibition activity of an iNOS gene, an enzyme involved in the production of NO during inflammatory response according to an embodiment of the present invention.
Figure 10:
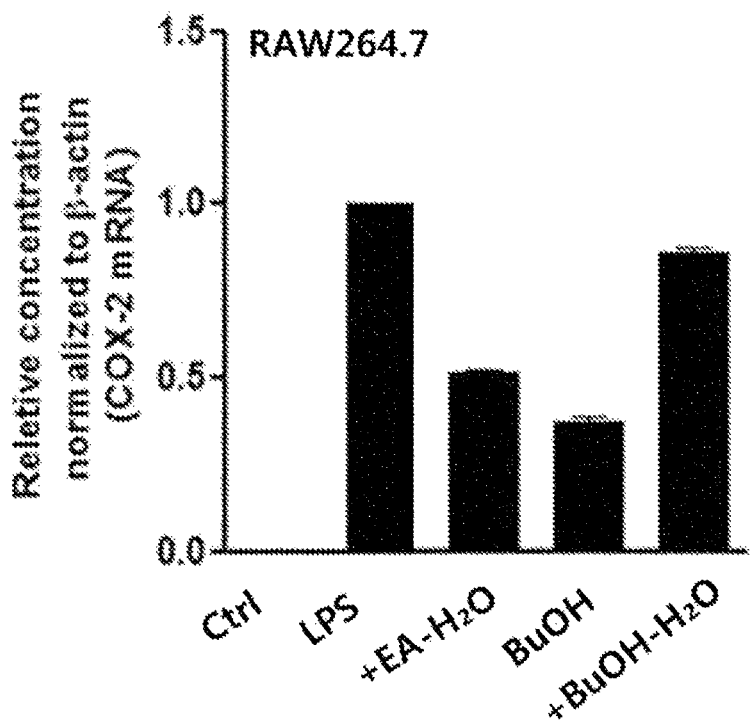
FIG. 10 is a graph which is obtained by observing the anti-inflammatory activity of an *S. fusiforme* fraction, and which demonstrates the expression inhibition activity of a COX-2 gene, an enzyme involved in the production of NO during inflammatory response according to an embodiment of the present invention.

As a result, all fractions except for the butanol-water fractions which were not found to have butanoic acid, effectively suppressed the production of nitric acid and this was almost the same results found when 25 μmol/L of L-NMMA (nitric oxide synthase inhibitor) was in presence. According to the results above, it has been demonstrated that since the *S. fusiforme* fraction containing butanoic acid removed nitric oxide or suppressed the production thereof, the concentration level of nitric oxide, an inflammatory mediator, could be controlled at the cellular level (FIG. 5).

4-2: Anti-Inflammatory Activity

The anti-inflammatory activity of the *S. fusiforme* fraction according to an embodiment of the present invention was examined at the cellular level by using Raw 264.7.

Specifically, Raw 264.7 cells were dispensed to a 6-well tissue culture plate, and pre-incubated at a temperature of 37° C. for 12 hours for the cells to be stably attached. Then, the cells were washed with PBS, and cultured for 24 hours after 1% FBS DMEM containing samples [lipopolysaccharide (LPS), each fraction (50 μg/mL)] was refilled. After the reaction was complete, the incubation media was removed, and total RNA was extracted according to the manual of a manufacturer after 1 mL of TRIZOL (Invitrogen, US) was put into each well.

With respect to cDNA synthesis, reverse transcription was conducted after creating a condition where the total amount reached 20 μL by using 1 μg of total RNA, Improm-II Reverse Transcription System (Promega, US) and an oligo dT primer, and then PCR was conducted by using primers (Bioneer, Korea) shown in Table 1 below.

A quantitative real-time PCR was conducted by using Rotor-Gene 6000 (Corbett Research, Australian) after mixing reactants to reach 20 μL in total by using a SYBR Green PCR master mix (Qiagen, US). A quantitative real-time PCR master mix was a mixture of 10 μL of 2× enzyme master mix, 7.0 μL of RNase-free distilled water, 1 μL (10 μM) of each primer, and 1 μL of cDNA template, and an each cycle of PCR included 10 minutes of pre-incubation at 95° C., 15 seconds of denaturation at 95° C., 15 seconds of annealing at 52° C., and 10 seconds of polymerization at 72° C., and this cycle was repeated 45 times. A melting curve analysis was used to identify the structure of an expected quantitative real-time PCR product while the size of the quantitative real-time PCR product was identified through electrophoresis on 1.2% agarose gel. An inter-run calibrator was used for a standard curve for the quantitative real-time PCR results of each gene, the gene expression level of each sample was measured by using Rotor-Gene 6000 Series Software 1.7, and the variations of other gene amplification were calibrated by relatively comparing the expression of β-actin.

As a result, it has been found that the *S. fusiforme* fraction decreased LPS-stimulated proinflammatory cytokine (IL-1β, IL-6, and TNF-α) gene expression of the Raw 264.7 cells and no cytotoxicity was found (FIGS. 6 to 10). In addition, it has been demonstrated that the butanoic acid-containing *S. fusiforme* extract has atopic-dermatitis-relieving efficacy as the inhibitory activity of pro-inflammatory genes, iNOS and COX-2, which are enzymes involved in the production of NO during inflammatory response, was expressed, and accordingly the butanoic acid-containing *S. fusiforme* extract showed the anti-inflammatory activity of suppressing the production of the pro-inflammatory cytokine in the Raw 264.7 cells in which an inflammatory reaction was induced through LPS. All information on primers used in the present invention is described in Table 1 below.

TABLE 1

| Primer | | Base sequence | SEQ ID NO. | Size (bp) | Accession No. |
|---|---|---|---|---|---|
| iNOS | Forward | 5'-TGCCCCTGGAAGTTTCTCTT-3' | 1 | 252 | NM_010927 |
| | Reverse | 5'-ACTGCCCCAGTTTTTGATCC-3' | 2 | | |
| IL-1β | Forward | 5'-GTGTCTTTCCCGTGGACCTT-3' | 3 | 107 | XM_006498795 |
| | Reverse | 5'-ATGGGAACGTCACACACCAG-3' | 4 | | |
| IL-6 | Forward | 5'-TCCATCCAGTTGCCTTCTTG-3' | 5 | 163 | NM_031168 |
| | Reverse | 5'-CCACGATTTCCCAGAGAACA-3' | 6 | | |
| TNFα | Forward | 5'-GATTATGGCTCAGGGTCCAA-3' | 7 | 179 | NM_013693 |
| | Reverse | 5'-GAGACAGAGGCAACCTGACC-3' | 8 | | |
| COX-2 | Forward | 5'-TTGCTGTACAAGCAGTGGCA-3' | 9 | 121 | NM_011198 |
| | Reverse | 5'-GCAGCCATTTCCTTCTCTCC-3' | 10 | | |
| IL-2 | Forward | 5'-AGCTCTACAGCGGAAGCACA-3' | 11 | 236 | NM_008366 |
| | Reverse | 5'-GTCAAATCCAGAACATGCCG-3' | 12 | | |
| IFN-γ | Forward | 5'-TGAAAATCCTGCAGAGCCAG-3' | 13 | 193 | NM_008337 |
| | Reverse | 5'-TGGACCTGTGGGTTGTTGAC-3' | 14 | | |

TABLE 1-continued

| Primer | | Base sequence | SEQ ID NO. | Size (bp) | Accession No. |
|---|---|---|---|---|---|
| IL-4 | Forward | 5'-ATATCCACGGATGCGACAAA-3' | 15 | 252 | M25892 |
| | Reverse | 5'-AAGCCCGAAAGAGTCTCTGC-3' | 16 | | |
| β-actin | Forward | 5'-TACAGCTTCACCACCACAGC-3' | 17 | 187 | NM_007393 |
| | Reverse | 5'-AAGGAAGGCTGGAAAAGAGC-3' | 18 | | |

Example 5: Expression of Th1/Th2 Cytokine mRNA Through Quantitative Real-Time PCR The quantitative real-time PCR was performed to conduct the comparison analysis of the mRNA expression of Th1/Th2 cytokine depending on treatment with the S. fusiforme fraction of the present invention.

Specifically, the spleen removed from the BALB/c mice was comminuted in mechanical way under cold phosphate buffered saline of pH 7.2 and a single spleen cell was obtained. After the purity of the spleen cell was maximized by removing red blood cells from the spleen tissue by using of an ammonium chloride-containing red blood cell lysis buffer solution (eBioscience, US), the spleen cell of the maximized purity was incubated in 10% fetal bovine serum-containing RPMI1640 complete media (hyclone, US), dispensed to a 12-well plate with $1 \times 10^7$ cells/ml and maintained under 5% $CO_2$ concentration and 37° C. incubation conditions. After 2 hours of stabilization passed, each fraction (ethanol, ethyl acetate, ethyl acetate-water, butanol and butanol-water) was pre-treated for 24 hours, followed by adding anti-CD3 monoclonal antibody (anti-CD3) for T-cell dependent stimuli and inducing reaction. Total RNA of the spleen cell stimulated by the anti-CD3 antibody (in vitro) was extracted by using a TRIZOL procedure (Invitrogen, US). With respect to cDNA synthesis, reverse transcription was conducted after creating a condition where the total amount reached 20 μL by using 1 μg of the total RNA, Improm-II Reverse Transcription System (Promega, US), and an oligo dT primer, and then PCR was conducted by using primers (Bioneer, Korea) shown in Table 1 above. A quantitative real-time PCR (quantitative real-time PCR) was conducted by using Rotor-Gene 6000 (Corbett Research, Australian) after mixing reactants until they reached 20 μL in total by using a SYBR Green PCR master mix (Qiagen, US). A quantitative real-time PCR master mix mixed 10 μL of 2× enzyme master mix, 7.0 μL of RNase-free distilled water, 1 μL (10 μM) of each primer and 1 μL of cDNA template, and an each cycle of PCR included 10 minutes of pre-incubation at 95° C., 15 seconds of denaturation at 95° C., 15 seconds of annealing at 52° C., and 10 seconds of polymerization at 72° C., and this cycle was repeated 45 times. A melting curve analysis was used to identify the structure of an expected quantitative real-time PCR product while the size of the quantitative real-time PCR product was identified through electrophoresis on 1.2% agarose gel. An inter-run calibrator was used for a standard curve against the quantitative real-time PCR results of each gene while the gene expression level of each sample was measured by using Rotor-Gene 6000 Series Software 1.7, and the variations of other gene amplification were calibrated by relatively comparing the expression of β-actin. The expression level of specimen was expressed as a percentage compared to the control gene, and a verification exercise was undertaken to check whether T cell receptor-mediated Th1/Th2 cytokine expression was continuously suppressed by each fraction at the cellular level in the spleen cell activated by the anti-CD3 antibody. The expression level of IL-2, IFN-γ and IL-4 mRNA was identified at 50 μg/mL concentration of each fraction, cyclosporine A (CsA) was used as a positive control, and the results were expressed as the average±standard deviation after the examination was repeated three times.

Figure 11:
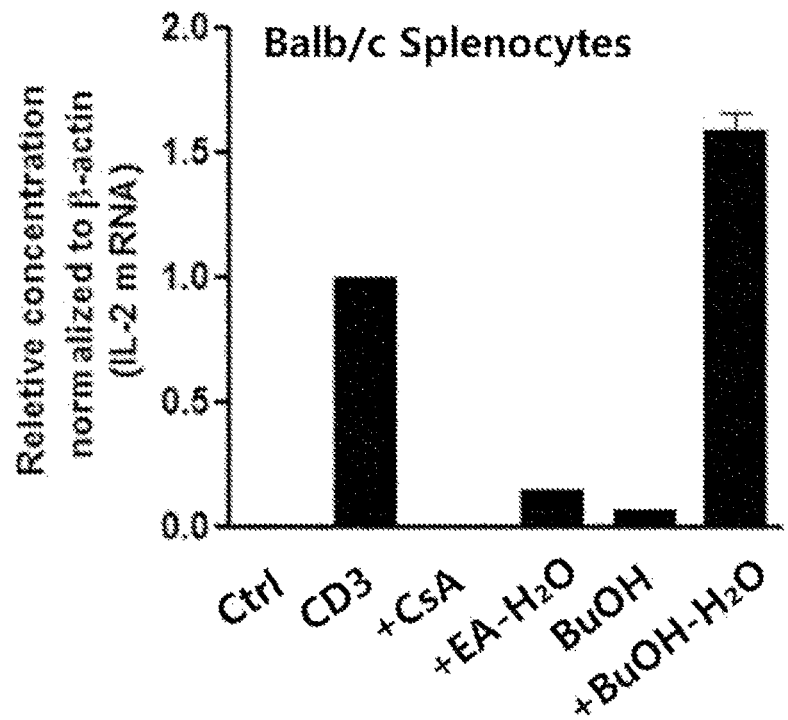
FIG. 11 is a graph which demonstrates the expression inhibition activity of an IL-2 gene through quantitative real-time PCR to examine the anti-atopic dermatitis effects of an *S. fusiforme* fraction according to an embodiment of the present invention.
Figure 12:
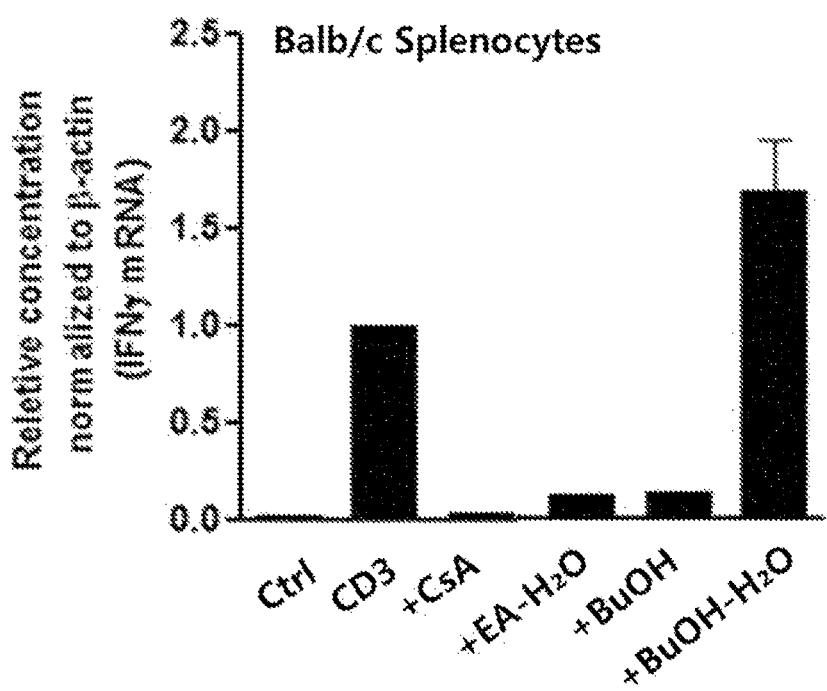
FIG. 12 is a graph which demonstrates the expression inhibition activity of an IFNγ gene through quantitative real-time PCR to examine the anti-atopic dermatitis effects of an *S. fusiforme* fraction according to an embodiment of the present invention.
Figure 13:
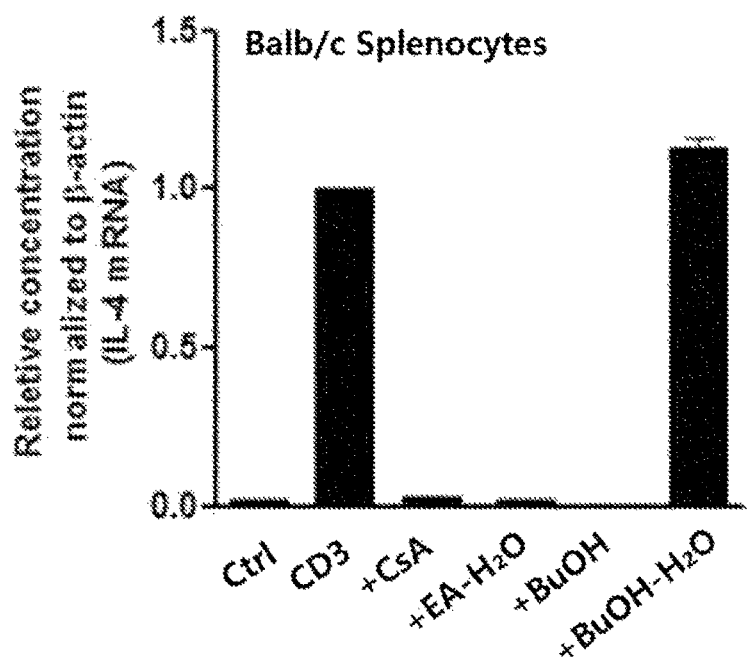
FIG. 13 is a graph which demonstrates the expression inhibition activity of an IL-4 gene through quantitative real-time PCR to examine the anti-atopic dermatitis effects of an *S. fusiforme* fraction according to an embodiment of the present invention.
Figure 14:
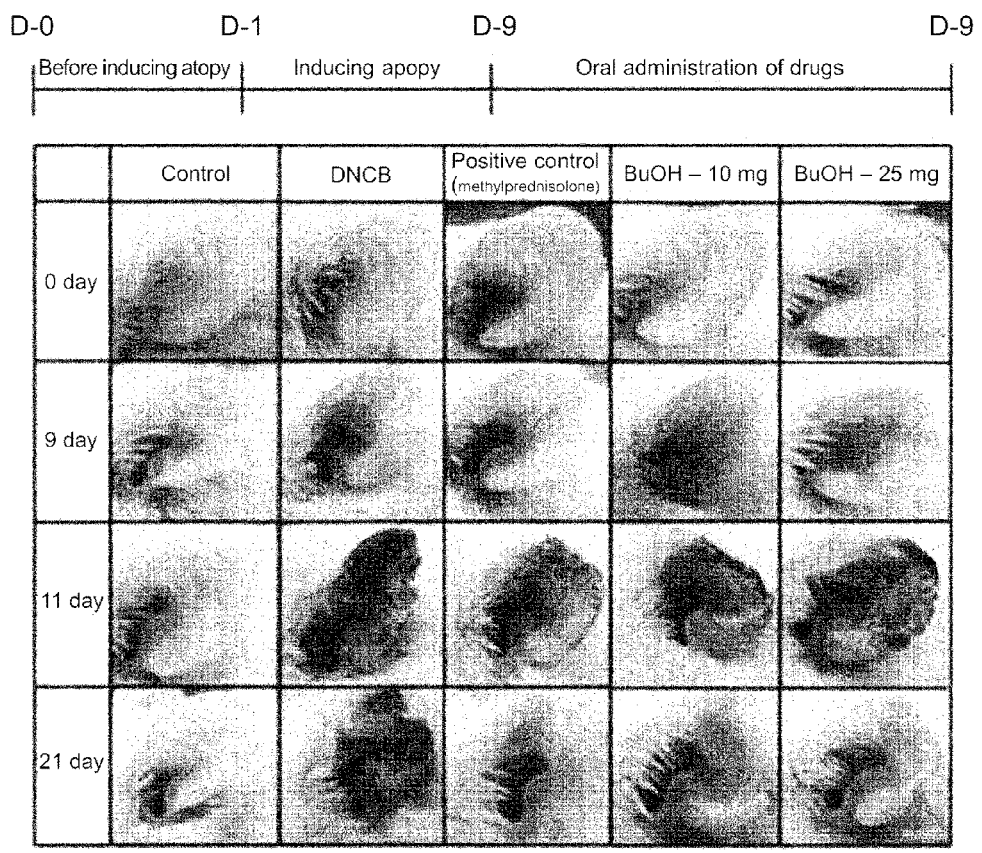
FIG. 14 is a photograph examining the proceedings of BALB/c mice induced to develop skin diseases similar to atopic dermatitis after administering to the mice an *S. fusiforme* fraction according to an embodiment of the present invention.

As a result, the T cells were highly activated during treatment with the anti-CD3 antibody, whereas the amount of IL-2, IFNγ and IL-4 mRNA expressed significantly decreased during treatment with 50 μg/mL of all fractions except for the butanol-water fraction in which butanoic acid was not found, and the gene suppression level by control was found to correspond to the area values of butanoic acid. The above results clearly and generally demonstrated the anti-atopic dermatitis effects of the butanoic acid contained in S. fusiforme (FIGS. 11 to 13).

Example 6: Histological Analysis of Mice Induced to Develop Atopic Dermatitis Caused by DNCB Treatment Histological analysis was conducted after the mice induced to develop atopic dermatitis was treated with the S. fusiforme fraction of the present invention.

Specifically, after 7-week old male BALB/c mice (Central Lab. Animal Inc. Korea) were purchased and then were housed in the laboratory for a week under the conditions (20±2° C. of room temperature, 50% of relative humidity, 12-hour light/dark cycle) so that they were adapted to the laboratory conditions. To make the BALB/c mice develop skin disorders similar to atopic dermatitis, both ears thereof were applied with 20 μg of 1% dinitrochlorobenzene (DNCB) (Sigma-Aldrich, US) which is dissolved in acetone for 9 days to induce a primary sign of hypersensitivity, and then were additionally applied with 20 μg of 0.5% DNCB for 3 weeks every 2 days to induce a secondary sign of hypersensitivity. In addition, while inducing the secondary sign of hypersensitivity, 0.5 mg/kg of Methylprednisolone was set as negative and positive controls each while the butanol fraction suspended in physiological saline (10, 25 mg/kg) was set as experimental groups, and they were orally administered at a set time (FIG. 4). On the last day, no treatment with the specimens was made, and the additional analysis of skin, after the enucleation thereof, was conducted. The ears of BALB/c mice enucleated during the atopic dermatitis-causing animal experiment above were fixed by 10% neutral buffered formalin, paraffin-embedded and sectioned as a sample having a section of 5 μm, and this sample was double strained with hematoxylin-eosin (H&E) and the thickness of the skin sample, the degree of cell penetration, etc. were measured. The examples and images of the present invention were taken in a dark room using Eclips Ti-S inverted microscope (Nikon, Japan) with an enlargement ratio of 200×.

Figure 15:
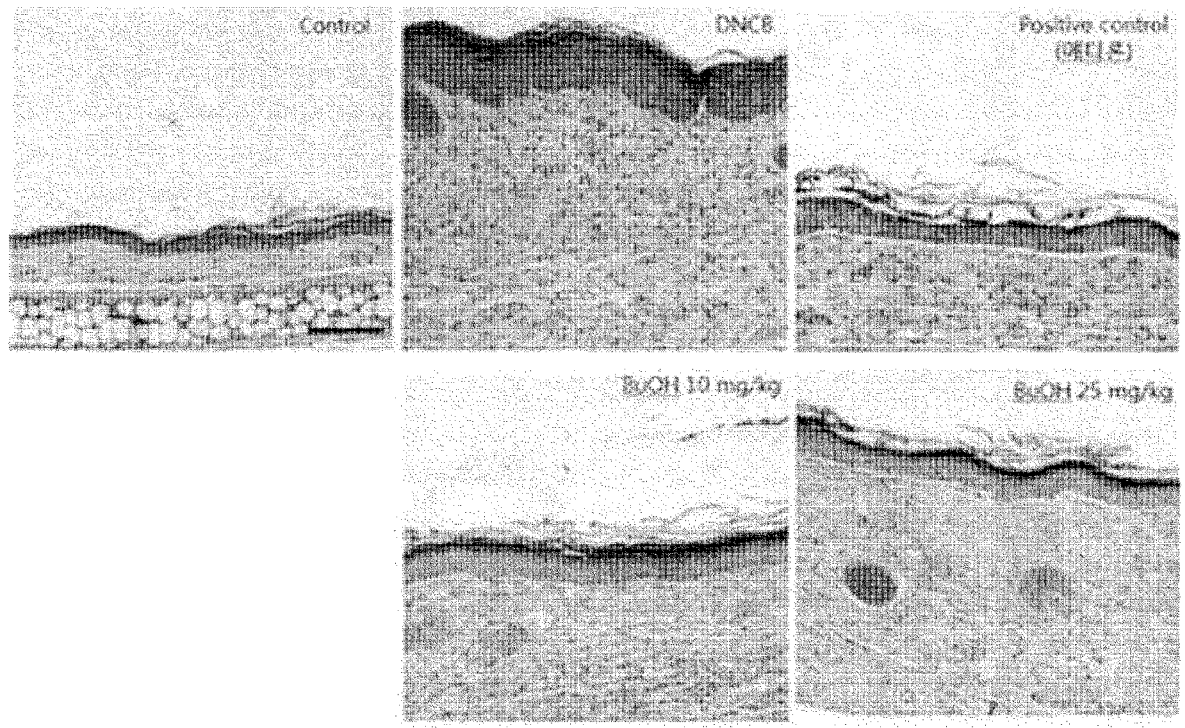
FIG. 15 is a photograph illustrating the histological analysis results of the ear of BALB/c mice induced to develop skin diseases similar to atopic dermatitis after the ear excised and stained according to an embodiment of the present invention.
Figure 16:
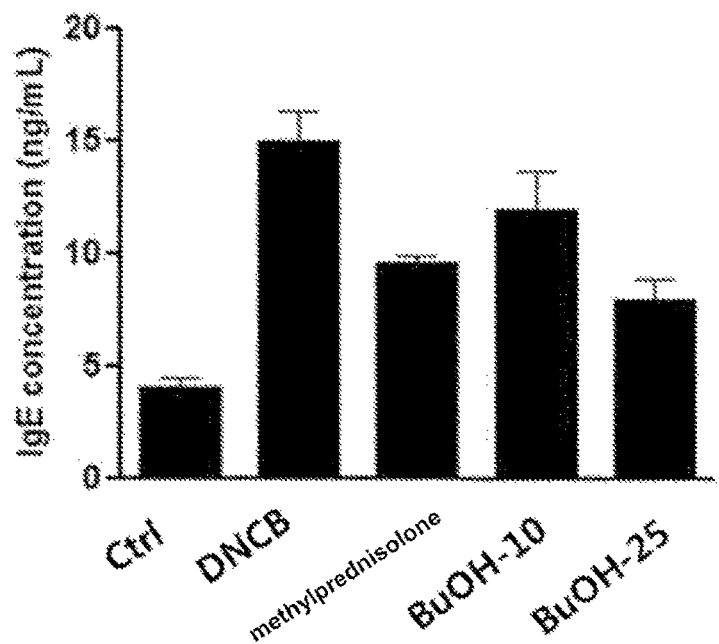
FIG. 16 is a graph illustrating the measurement results of blood IgE level which is related to the itchiness of BALB/c mice induced to develop skin diseases similar to atopic dermatitis according to an embodiment of the present invention.
Figure 17:
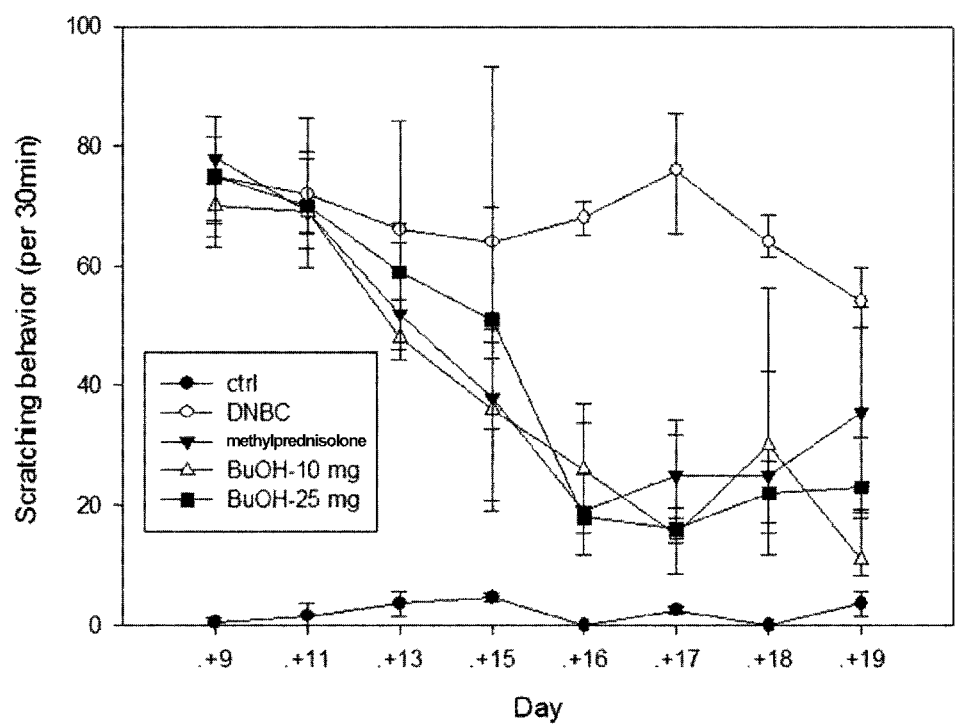
FIG. 17 is a graph illustrating the measurement results of ear-scratching behavior of BALC/c mice induced to develop skin diseases similar to atopic dermatitis according to an embodiment of the present invention.

As a result, when comparing the group treated with DNCB to the normal control group, the skin of the DNCB-treated group had thicker skin while that of the positive control (Methylprednisolone) and the group treated with the butanol fraction had thinner skin (FIG. 15). In particular, the group treated with the butanol fraction including a large amount of a high concentration of butanoic acid was much better than the PC treatment group, as the positive control, in terms of skin tissue conditions, which is expected to provide more effective recovery from skin disorders similar to atopic dermatitis. Furthermore, according to the results of blood IgE level which is related to itchiness due to atopic dermatitis, the high concentration of butanol fraction (25 mg/kg) was found to have an efficacy equivalent to that of the positive control, Methylprednisolone (FIG. 16), and also was found to have an efficacy equivalent to or better than that of the positive group in terms of the ear-scratching behavior during the oral administration (FIG. 17).

Example 7: *S. fusiforme* Extract Activity Measurement

To measure the activity of the final sample of the present invention, an open column chromatography as conducted under a condition of a ratio of n-hexane to ethyl acetate=8:2 and the sample was divided into a fraction 1, a fraction 2 and a fraction 3 (F1-F3) based on the spot of thin-layer chromatography (TLC). The activity of an atopic dermatitis-causing factor was examined by using the fractions above.

As a result, the gene expression of interleukin-2 (IL-2), interferon γ (IFNγ) and interleukin-4 (IL-4) was significantly reduced in the F2 fraction, thus indicating that components present in the F2 contained major active ingredients of the *S. fusiforme*, and the CD25 gene, an early activation marker of immune cells (T cells) was also significantly reduced, demonstrating the anti-atopic dermatitis effects (FIGS. 19-22). In addition, eight spots were identified in the F2 TLC results, and an Rf value of each spot was 0.12, 0.33, 0.43, 0.49, 0.60, 0.65, 0.79 and 0.88. The Rf value of the F1 and F2 was 0.98 and 0.12 respectively.

The present invention is described with reference to the described examples, but the examples are merely illustrative. Therefore, it will be understood by those skilled in the art that various modifications and other equivalent embodiments can be made from the described embodiments. Hence, the real protective scope of the present invention shall be determined by the technical scope of the accompanying claims.

The invention claimed is:

1. A method of treating atopic dermatitis in a subject suffering atopic dermatitis comprising administering a therapeutically effective dose of a butanol fraction of a *Sargassum fusiforme* (*S. fusiforme*) extract to the subject,
   wherein the butanol fraction is prepared by a method comprising:
   i) preparing *S. fusiforme* lower alcohol extract by extracting *S. fusiforme* with an extraction solvent comprising a lower alcohol having 1 to 4 carbon atoms, to produce the *S. fusiforme* lower alcohol extract;
   ii) dissolving the *S. fusiforme* lower alcohol extract into water to produce an aqueous solution and fractionating aqueous solution with ethyl acetate to produce a water layer;
   iii) fractionating the water layer fractionated in the step ii with butanol; and
   iv) preparing the butanol fraction by removing butanol from a fractionated butanol layer in the step iii.

2. The method of claim 1, wherein the volume ratio of the aqueous solution of the *S. fusiforme* lower alcohol extract to the ethyl acetate is 1 to 0.5-2.

3. The method of claim 1, wherein the volume ratio of the water layer to the butanol is 1 to 0.5-2.

4. The method of claim 3, wherein the administering is performed by oral, intravenous, intramuscular or dermal administration.

\* \* \* \* \*

SEQUENCE LISTING

<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: iNOS  F

<400> SEQUENCE: 1
tgcccctgga agtttctctt                                              20

<210> SEQ ID NO 2
<211> LENGTH: 20
<212> TYPE: DNA
<213> ORGANISM: Artificial Sequence
<220> FEATURE:
<223> OTHER INFORMATION: iNOS  R

<400> SEQUENCE: 2
actgccccag tttttgatcc                                              20

<210> SEQ ID NO 3
<211> LENGTH: 20
<212> TYPE: DNA
<213> ORGANISM: Artificial Sequence
<220> FEATURE:
<223> OTHER INFORMATION: IL-1beta  F

<400> SEQUENCE: 3
gtgtctttcc cgtggacctt                                              20

<210> SEQ ID NO 4
<211> LENGTH: 20
<212> TYPE: DNA
<213> ORGANISM: Artificial Sequence
<220> FEATURE:
<223> OTHER INFORMATION: IL-1beta  R

<400> SEQUENCE: 4

-continued atgggaacgt cacacaccag                                               20

<210> SEQ ID NO 5
<211> LENGTH: 20
<212> TYPE: DNA
<213> ORGANISM: Artificial Sequence
<220> FEATURE:
<223> OTHER INFORMATION: IL-6  F

<400> SEQUENCE: 5
tccatccagt tgccttcttg                                               20

<210> SEQ ID NO 6
<211> LENGTH: 20
<212> TYPE: DNA
<213> ORGANISM: Artificial Sequence
<220> FEATURE:
<223> OTHER INFORMATION: IL-6  R

<400> SEQUENCE: 6
ccacgatttc ccagagaaca                                               20

<210> SEQ ID NO 7
<211> LENGTH: 20
<212> TYPE: DNA
<213> ORGANISM: Artificial Sequence
<220> FEATURE:
<223> OTHER INFORMATION: TNF alpha  F

<400> SEQUENCE: 7
gattatggct cagggtccaa                                               20

<210> SEQ ID NO 8
<211> LENGTH: 20
<212> TYPE: DNA
<213> ORGANISM: Artificial Sequence
<220> FEATURE:
<223> OTHER INFORMATION: TNF alpha  R

<400> SEQUENCE: 8
gagacagagg caacctgacc                                               20

<210> SEQ ID NO 9
<211> LENGTH: 20
<212> TYPE: DNA
<213> ORGANISM: Artificial Sequence
<220> FEATURE:
<223> OTHER INFORMATION: COX-2  F

<400> SEQUENCE: 9
ttgctgtaca agcagtggca                                               20

<210> SEQ ID NO 10
<211> LENGTH: 20
<212> TYPE: DNA
<213> ORGANISM: Artificial Sequence
<220> FEATURE:
<223> OTHER INFORMATION: COX-2  R

<400> SEQUENCE: 10
gcagccattt ccttctctcc                                               20

<210> SEQ ID NO 11
<211> LENGTH: 20
<212> TYPE: DNA
<213> ORGANISM: Artificial Sequence

```
<220> FEATURE:
<223> OTHER INFORMATION: IL-2  F

<400> SEQUENCE: 11
agctctacag cggaagcaca                                               20

<210> SEQ ID NO 12
<211> LENGTH: 20
<212> TYPE: DNA
<213> ORGANISM: Artificial Sequence
<220> FEATURE:
<223> OTHER INFORMATION: IL-2  R

<400> SEQUENCE: 12
gtcaaatcca gaacatgccg                                               20

<210> SEQ ID NO 13
<211> LENGTH: 20
<212> TYPE: DNA
<213> ORGANISM: Artificial Sequence
<220> FEATURE:
<223> OTHER INFORMATION: IFN-gamma  F

<400> SEQUENCE: 13
tgaaaatcct gcagagccag                                               20

<210> SEQ ID NO 14
<211> LENGTH: 20
<212> TYPE: DNA
<213> ORGANISM: Artificial Sequence
<220> FEATURE:
<223> OTHER INFORMATION: IFN-gamma  R

<400> SEQUENCE: 14
tggacctgtg ggttgttgac                                               20

<210> SEQ ID NO 15
<211> LENGTH: 20
<212> TYPE: DNA
<213> ORGANISM: Artificial Sequence
<220> FEATURE:
<223> OTHER INFORMATION: IL-4  F

<400> SEQUENCE: 15
atatccacgg atgcgacaaa                                               20

<210> SEQ ID NO 16
<211> LENGTH: 20
<212> TYPE: DNA
<213> ORGANISM: Artificial Sequence
<220> FEATURE:
<223> OTHER INFORMATION: IL-4  R

<400> SEQUENCE: 16
aagcccgaaa gagtctctgc                                               20

<210> SEQ ID NO 17
<211> LENGTH: 20
<212> TYPE: DNA
<213> ORGANISM: Artificial Sequence
<220> FEATURE:
<223> OTHER INFORMATION: Beta-actin  F

<400> SEQUENCE: 17
tacagcttca ccaccacagc                                               20
```

```
<210> SEQ ID NO 18
<211> LENGTH: 20
<212> TYPE: DNA
<213> ORGANISM: Artificial Sequence
<220> FEATURE:
<223> OTHER INFORMATION: Beta-actin  R

<400> SEQUENCE: 18
aaggaaggct ggaaaagagc                                                       20
```